(12) United States Patent
Basler et al.

(10) Patent No.: US 8,893,387 B2
(45) Date of Patent: Nov. 25, 2014

(54) METHOD FOR PRODUCING A DENTAL SHAPED PART

(75) Inventors: Franz Basler, Laudenbach (DE); Peter Fornoff, Reichelsheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 182 days.

(21) Appl. No.: 13/271,790

(22) Filed: Oct. 12, 2011

(65) Prior Publication Data
US 2012/0029682 A1 Feb. 2, 2012

Related U.S. Application Data

(62) Division of application No. 10/557,153, filed as application No. PCT/EP2004/051398 on Jul. 7, 2004, now Pat. No. 8,057,912.

(30) Foreign Application Priority Data

Jul. 7, 2003 (DE) .................................. 103 30 758

(51) Int. Cl.
*A61C 5/10* (2006.01)
*A61C 13/00* (2006.01)

(52) U.S. Cl.
CPC ... *A61C 13/0022* (2013.01); *G05B 2219/37227* (2013.01); *A61C 13/0003* (2013.01)
USPC .............. 29/896.1; 29/557; 29/558; 433/223; 433/72; 433/201.1; 451/5; 451/9

(58) Field of Classification Search
CPC ........... A61C 13/0022; A61C 13/0003; A61C 13/0006; B23Q 17/20; G05B 2219/37227
USPC ............. 29/896.1, 896.11, 557, 558; 433/72, 433/201.1, 202.1, 203.1, 223; 451/5, 9, 28, 451/54, 58; 700/116, 118
See application file for complete search history.

(56) References Cited

U.S. PATENT DOCUMENTS

| 3,665,493 A | 5/1972 | Glowzewski et al. |
| 4,615,678 A | 10/1986 | Moermann et al. ........ 433/201.1 |

(Continued)

FOREIGN PATENT DOCUMENTS

| AU | 762679 B2 | 7/2003 |
| CA | 2 322 761 A1 | 9/1999 |

(Continued)

OTHER PUBLICATIONS

Brian K.S. Kucey et al., "The Procera Abutment—The Fifth Generation Abutment for Dental Implants," Journal of Canadian Dental Association, vol. 66, No. 8, pp. 445-449 (Sep. 2000).

(Continued)

*Primary Examiner* — Sarang Afzali
(74) *Attorney, Agent, or Firm* — Fitzpatrick, Cella, Harper & Scinto

(57) ABSTRACT

A method for producing a dental shaped part includes checking an outer contour of a tool of machining equipment, using least one gauge provided on a blank formed from a tooth restoration material from which a dental shaped part is to be machined using the machining equipment. The method also includes machining the dental shaped part from the blank using the tool of the machining equipment, when the outer contour of the tool corresponds to the at least one gauge provided on the blank.

14 Claims, 8 Drawing Sheets

(56) References Cited

U.S. PATENT DOCUMENTS

| | | | |
|---|---|---|---|
| 4,988,297 A | 1/1991 | Lazzara et al. | |
| 5,092,022 A | 3/1992 | Duret | |
| 5,273,429 A | 12/1993 | Rekow et al. | |
| 5,342,696 A | 8/1994 | Eidenbenz et al. | 428/542.8 |
| 5,359,511 A | 10/1994 | Schroeder et al. | |
| 5,378,091 A | 1/1995 | Nakamura | |
| 5,556,278 A | 9/1996 | Meitner | |
| 5,716,215 A | 2/1998 | Blacklock | |
| 5,788,494 A | 8/1998 | Phimmasone | |
| 5,846,079 A | 12/1998 | Knode | |
| 5,989,029 A | 11/1999 | Osorio et al. | |
| 6,126,445 A | 10/2000 | Willoughby | |
| 6,142,782 A | 11/2000 | Lazarof | |
| 6,224,371 B1 | 5/2001 | De Luca | |
| 6,231,342 B1 | 5/2001 | Osorio et al. | |
| 6,354,836 B1 | 3/2002 | Panzera et al. | |
| 6,394,880 B1 | 5/2002 | Basler et al. | |
| 6,398,554 B1 | 6/2002 | Perot et al. | |
| 6,482,284 B1 * | 11/2002 | Reidt et al. | 156/200 |
| 6,485,305 B1 | 11/2002 | Pfeiffer | |
| 6,627,327 B2 * | 9/2003 | Reidt et al. | 428/577 |
| 6,640,150 B1 | 10/2003 | Persson et al. | |
| 6,666,684 B1 | 12/2003 | Names | |
| 6,788,986 B1 | 9/2004 | Traber et al. | |
| 6,968,247 B2 | 11/2005 | Rathke et al. | |
| 6,970,760 B2 | 11/2005 | Wolf et al. | |
| 7,086,863 B2 | 8/2006 | Van der Zel | |
| 7,226,338 B2 | 6/2007 | Duncan et al. | |
| 8,057,912 B2 | 11/2011 | Basler et al. | 428/542.8 |
| 2002/0018980 A1 | 2/2002 | Yeung | |
| 2002/0090592 A1 | 7/2002 | Rilet et al. | 433/173 |
| 2003/0073394 A1 | 4/2003 | Reidt et al. | |
| 2006/0106484 A1 | 5/2006 | Saliger et al. | |
| 2006/0141250 A1 | 6/2006 | Basler et al. | |
| 2006/0292527 A1 | 12/2006 | Basler et al. | 433/213 |
| 2007/0050072 A1 | 3/2007 | Schwotzer | |
| 2009/0273108 A1 | 11/2009 | Koebel et al. | |

FOREIGN PATENT DOCUMENTS

| | | |
|---|---|---|
| DE | 196 54 055 A1 | 6/1998 |
| DE | 197 33 161 A1 | 2/1999 |
| DE | 10 2004 063 417 A1 | 7/2006 |
| DE | 10 2006 052 027 A1 | 5/2008 |
| EP | 0 455 854 A1 | 11/1991 |
| EP | 0 850 601 A2 | 7/1998 |
| EP | 0 904 743 A2 | 3/1999 |
| EP | 1 023 876 A2 | 8/2000 |
| EP | 1 062 916 A1 | 12/2000 |
| EP | 1 252 867 A1 | 10/2002 |
| EP | 1 067 880 A1 | 10/2003 |
| EP | 1 658 825 A1 | 5/2006 |
| JP | 10277059 A | 10/1998 |
| WO | 9913796 A1 | 3/1999 |
| WO | 0135854 A1 | 5/2001 |
| WO | 03007834 A1 | 1/2003 |
| WO | 03024352 A1 | 3/2003 |
| WO | 2004060197 A1 | 7/2004 |
| WO | 2005002463 A1 | 1/2005 |

OTHER PUBLICATIONS

European Patent Office, "Internationaler Vorlaufiger Bericht Uber Die Patentierbarkeit" issued in International Application No. PCT/EP2008/060043, 6 pages, Oct. 19, 2009 (and English translation thereof).

European Patent Office, "Schriftlicher Bescheid Der Internationalen Recherchenbehorde" in connection with International Application No. PCT/EP2009/053999, 6 pages, Oct. 3, 2010 (and English translation thereof).

At least partial English translation of Office Action issued Feb. 12, 2009, by the German Patent Office in connection with International Application No. PCT/EP2009/053999, 2 pages.

U.S. Patent and Trademark Office, Office Action dated Apr. 20, 2009, in connection with U.S. Appl. No. 10/557,153, 11 pages.

U.S. Patent and Trademark Office, Office Action dated Oct. 14, 2009, in connection with U.S. Appl. No. 10/557,153, 12 pages.

U.S. Patent and Trademark Office, Office Action dated Mar. 11, 2010, in connection with U.S. Appl. No. 10/557,153, 13 pages.

U.S. Patent and Trademark Office, Office Action dated Nov. 23, 2010, in connection with U.S. Appl. No. 10/557,153, 16 pages.

U.S. Patent and Trademark Office, Office Action dated Mar. 25, 2010, in connection with U.S. Appl. No. 11/304,536, 5 pages.

U.S. Patent and Trademark Office, Office Action dated Mar. 11, 2011, in connection with U.S. Appl. No. 11/304,536, 6 pages.

* cited by examiner

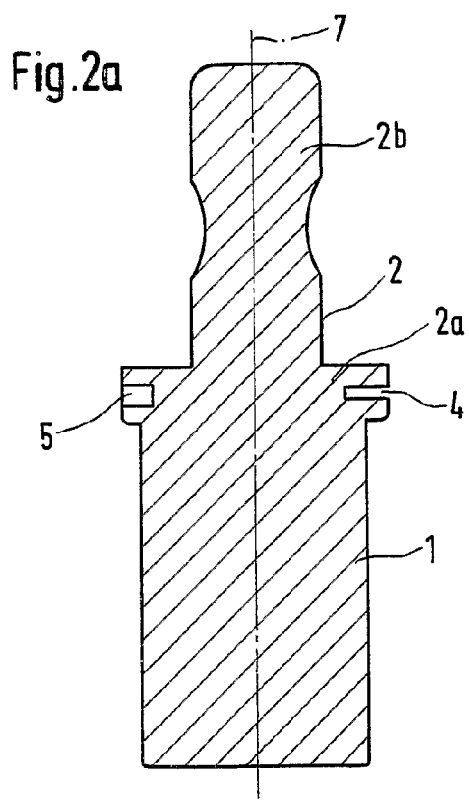
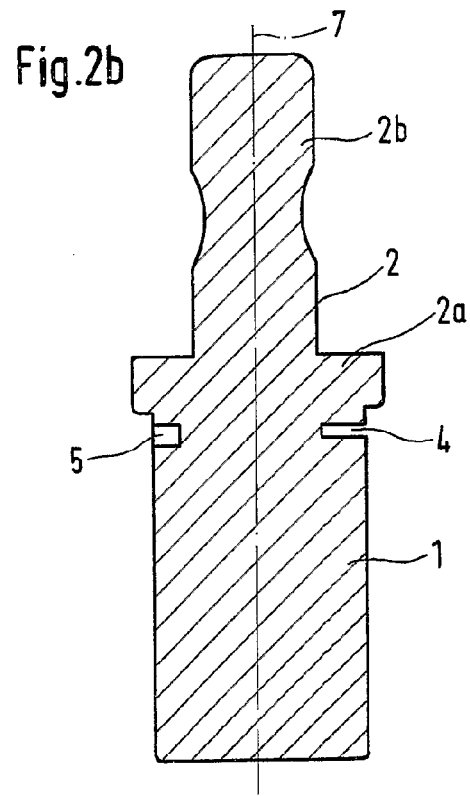
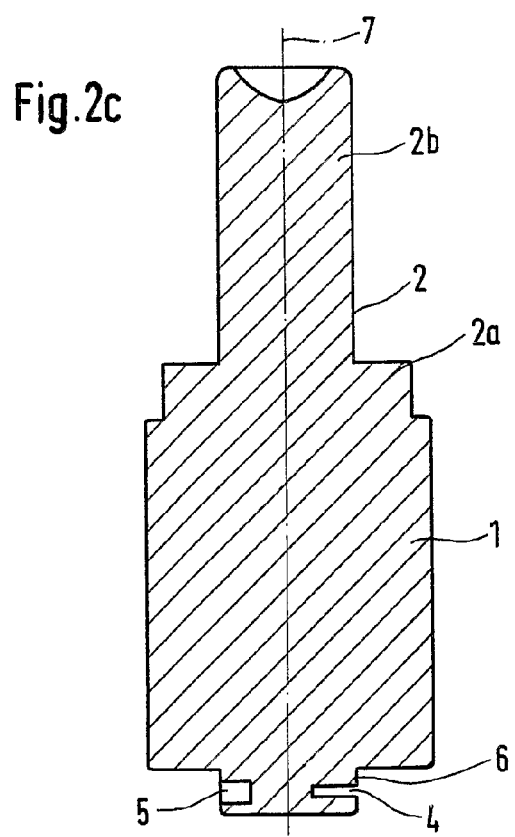

METHOD FOR PRODUCING A DENTAL SHAPED PART

CROSS-REFERENCE TO RELATED APPLICATIONS

This application is a division of U.S. patent application Ser. No. 10/557,153, filed Nov. 17, 2005, now U.S. Pat. No. 8,057,912, which is a national-stage entry of International Application No. PCT/EP2004/051398, filed Jul. 7, 2004, and which claims benefit under 35 U.S.C. §119 of German Patent Application No. 103 30 758.3, filed Jul. 7, 2003. The entire disclosure of each prior application is incorporated by reference in its entirety herein for all purposes

BACKGROUND OF THE INVENTION

The invention relates to a blank as defined in the generic clause of claim 1 which is to be used in the production of a dental shaped part, and to a method of producing said shaped part.

EP 0 160 797 discloses a blank for the production of dental shaped parts, which blank is made up of a handle and a corpus of different materials. A reference surface on the handle can be formed in such a way that control information for the machining process depending on the characteristics of the blank, can be derived.

Another blank for the production of dental shaped parts is disclosed by DE 196 12 699. Here again, recognition of the type of blank from the geometrical shape of its contours is disclosed.

EP 0 455 854 discloses a blank, from which there can be carved a mating part to be administered to the patient, on the one hand, and an additional retaining or supporting part, on the other hand. A recess is carved into the mating part, which is shaped in such a way that it can be fitted on the retaining or supporting part.

The position of the abrasion-prone tools used for machining the blank is adjusted such that the tools are moved to engage defined reference surfaces on the blank. These reference surfaces can be on the handle, as shown in EP 0 160 797 or they can, as shown in DE 196 12 699, be positioned on the corpus of the blank or on its own reference part, which is attached to the blank at more or less arbitrary places.

The reference surfaces that are provided in the prior art are only suitable for purposes of adjustment of the tool relative to the blank.

It is an object of the invention to make it possible to reliably analyze or identify the tool equipment and/or the type and state of wear of the tool used in the machining equipment employed for machining the blank. In particular, it is intended to provide means of recognizing incorrect tool setups in grinding machines using different types of tool at the same time.

SUMMARY OF THE INVENTION

This object is achieved, according to the invention, by the features defined in the claims, with certain developments being set forth in the respective subclaims.

The advantage of a blank for the fabrication of dental shaped parts, comprising a corpus of tooth restoration material, from which, in turn, the shaped part can be made by machining, with the blank exhibiting at least one gauge (also referred to herein as "gage") that is geometrically formed in such a way that the tool used for machining is identifiable on the basis of its outer contour by means of the at least one gage, is that the effectiveness of machining can thus be guaranteed using the intended specialty tool. Whether the blank consists of ceramics, metal, plastics, or any other dimensionally stable material is of no consequence. An incorrect tool setup can be particularly well recognized in the case of grinding machines that use different types of tool at the same time. Both grinding and milling, for example, are suitable machining processes.

The gage is advantageously assigned to an ideal outer contour of a first tool, as this makes it possible to identify the tool that corresponds to the gage. In addition, another tool having a different ideal outer contour from that of the first tool can be distinguished with the aid of the same gage. In this way, not only can the tool matching the gage be selected, but different tools can be distinguished from each other.

An advantageous shape of such a gage can be a recess, in which the ideal outer contour of the first tool engages. Such engagement can be made possible, for example, by forming the recess such that the tool having an ideal outer contour fits it exactly.

Advantageously, the gage exhibits a recess that corresponds to a first diameter d1 of the ideal outer contour of a first cylindrical tool, which diameter is smaller than the ideal outer contour of a second cylindrical tool having a second diameter d2. In this way, at least two tools of identical geometry but of different sizes can be distinguished from each other.

Another advantageous shape of such a recess serving as a gage is a recess that is tapered in correspondence with the ideal outer contour of a first tapered tool, with the recess tapering to a diameter that is smaller than the smallest diameter of the ideal outer contour of a second cylindrical tool. In this way, it is also possible to distinguish tools of different geometry from each other. This principle is naturally also transferable to any other tool shapes, and can be used, for example, on tools having a rounded end.

Advantageously, the gage is in the form of a groove or bore, since these are particularly easy to create.

It is especially advantageous when the gage is designed in such a way that when the tool to which the gage is assigned is moved into the gage, the actual state of the permissible allowances of the respective tool can be identified such that the degree of wear of the tool can be assessed and, for example, a certain minimum tool quality can be prescribed. A further advantage is that it is possible to effect a reliable analysis or identification of the tool setup and/or the type of tool used in the machining equipment employed for machining the blank, and the wear condition of said tool.

Another advantage is gained when the blank comprises a handle for mounting and/or positioning the corpus of the blank in a machining device and when the gage is provided on said handle, since thereby the gage will remain effective throughout the entire machining operation and the corresponding tools can be checked on a continuous basis. Such identification of poor quality tools or incorrect setups will be contributory, for example, to preventing tool fracture during machining.

Alternatively, at least one gage can be on the handle or on the corpus of the blank or on a reference area, by which means special production characteristics can be taken into consideration. In addition, at least one gage can be at at least two of the said positions.

If the gage is designed as a universal gage for prospective tools, advantageously various tool geometries can be checked with only one gage. A gage is considered to be a universal gage if the geometrical shape of several tools can be checked with the aid of this one gage. This requires that the shape geometry itself consists of several individual shape geometries, of which each corresponds to the tool geometry of its respective tool. By this means, it is not only possible for a more extensive tool setup to be examined with the aid of only one gage, but it is also possible to examine the degree of wear of a number of, or if necessary all, tools with the aid of just one gage. In this way, it will be possible to detect incorrect setup with minimum elaboration. Instead of using only one universal gage, several universal gages of identical or different geometrical shapes can be used if this would seem necessary, for production or control reasons for example, in order to enable the tool to be driven to the blank more quickly, for instance.

In accordance with a development, several gages are provided for the characterization of a single tool and this single tool can be examined for more than one parameter of its condition and in particular for its deviation from an ideal condition.

The advantage of a procedure for the fabrication of dental shaped parts using a blank corpus of dental restoration material, from which the entire shaped part can be carved in a machining device by means of a tool, and the profile of the tool selected for such machining is examined before it is put to use with the aid of at least one of the gages disposed on the blank is that it is possible to ensure, in this way, that said tool is, indeed, the correct tool for the machining operation to be carried out. This is achieved in that the actual values obtained are compared with the ideal outer contour.

A further advantage results if the tool dedicated to the gage is driven into the gage and the current deviation of the assigned tool from the ideal is determined, since information about the momentary tool condition can be determined in this manner each and every time the tool engages the gage(s). This can be done several times during an operation sequence. Thus an optimal condition and, therefore, high quality of the shaped part can be guaranteed.

Another advantage results when the degree of deviation of the actual condition of the tool from the ideal outer contour of the tool is determined and this deviation is allowed for when organizing the control of the blank machining operation. A parameter, for example, can be established for this purpose. A tool whose unsuitable condition has been recognized can, in such a case, be excluded from the machining process and new or other tools in better condition can carry out the task in hand. It is also conceivable to reduce down times by causing a change of tool to be suggested only if the machining process cannot be finished with any of the other tools that are already involved in the process. The information gained from the comparison can thus be used for a tool condition-specific control of the machining process.

All in all, it is to be emphasized that the gages can be positioned anywhere and, advantageously, are not only provided for the selection of the tool by reproducing the negative shape of the tool intended for machining in its ideal condition, but are also available for determining the wear condition of the tool. The exact position of the gage will be known to the machining equipment or is determined by it.

In addition, the gage can be designed such that it can identify tools that are designated for the material.

This can, for example, be effected via the geometry or a specific machining resistance when using the tool in the known geometry of the gage under known machining effort.

BRIEF DESCRIPTION OF THE DRAWINGS

The method of the invention is described with reference to the drawings, in which:

FIG. 2a is a longitudinal cross-section of the blank of FIG. 1a, FIG. 2b is a longitudinal cross-section of the blank of FIG. 1b, FIG. 2c is a longitudinal cross-section of the blank of FIG. 1c.

DESCRIPTION OF EXEMPLARY EMBODIMENTS OF THE INVENTION

Figure 1A:
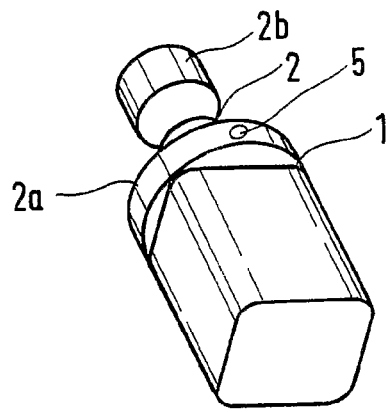
FIG. 1a is a perspective view of a first blank for the fabrication of a dental shaped part with a gage on a handle of a blank corpus.

The blank of FIG. 1a contains a corpus 1, which can consist of a material commonly used in dental technology, e.g. a ceramic material, but also of any other dimensionally stable material such as metal or plastics, from which the shaped part will be fabricated by means of a material removal machining process. The corpus 1 of the blank is advantageously circular or rectangular in cross section. The front end of the corpus of the blank is adjoined by a cylindrical handle 2 in known manner.

The material of handle 2 can be identical with, or different from, that of the corpus 1. In the case of different materials, blank corpus 1 will be fastened to handle 2, for example by gluing. For this purpose, handle 2 exhibits, for example, a circular cylindrical flange 2a having a diameter that is sufficient to ensure secure attachment to corpus 1, and a shaft 2b for insertion into the machining equipment. Shaft 2b is designed to fit into a predefined socket on the machining equipment.

Figure 1B:
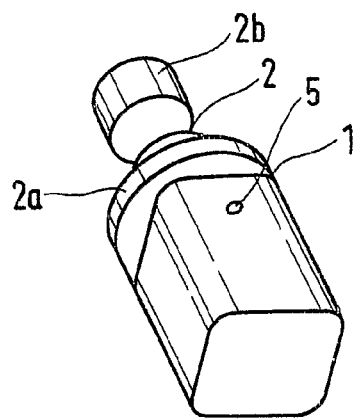
FIG. 1b is a perspective view of a further embodiment of a blank according to the invention with a gage on the blank corpus.
Figure 1C:
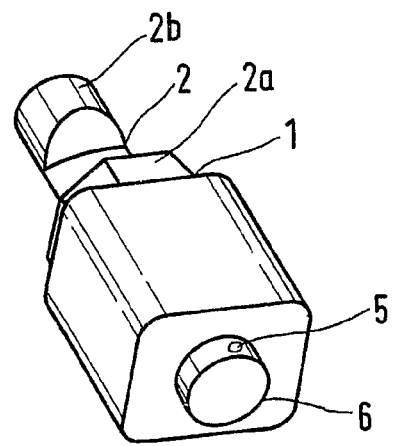
FIG. 1c is a perspective view of a further blank having at least one gage on a reference surface located on the blank.

In FIGS. 1a to c, a recess 5 having gage properties is provided. Such recesses can be provided individually or in moderate numbers at various places of the blank. Due to their gage properties, these recesses serve to select and evaluate the individual tools, since five specific sets of data of the tool, e.g. their dimensions, state of wear, and position, can be identified with the aid of the recesses 5.

The blanks illustrated in FIGS. 2a to 2c are structurally comparable to the blanks of FIGS. 1a to 1c. According to FIG. 2a, two gages 4, 5 are provided on flange 2a of handle 2 of the blank in the form of gage recesses. In this case, the gages are in the form of a groove and bore 4, 5 respectively. FIG. 2b shows a blank which exhibits two gages 4, 5 on the corpus 1 of the blank. The blank of FIG. 2c is also structurally comparable to the blank of FIG. 1c and comprises a mating part 6, which in this case is disposed on corpus 1 opposite handle 2. The mating part 6 can be of the same material as the corpus of the blank and can be located on the axis 7 of the handle and can itself serve to determine the size and position of the machining tool. Alternatively, any number of other locations can be considered for the mating part 6, as long as it does not impede the machining process. Moreover, it can have the cylindrical shape shown or some other shape. Two gages 4, 5 are disposed on mating part 6 in the form of recesses, which in this figure are in the form of a groove 4 and bore 5.

Figure 3A:
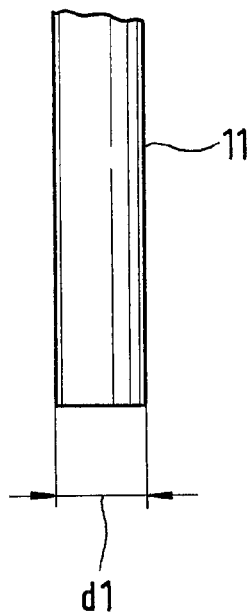
FIG. 3a shows a machining tool in the form of a diamond-coated cylindrical grinder having a first diameter.
Figure 3B:
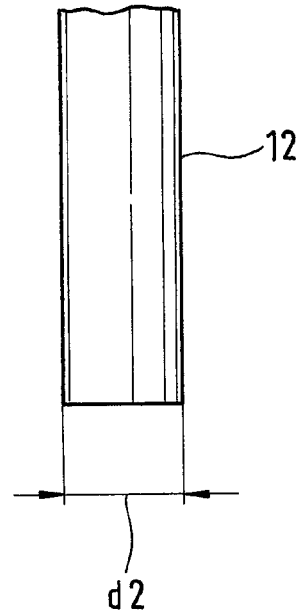
FIG. 3b shows a machining tool in the form of a diamond-coated cylindrical grinder having a second diameter.
Figure 3C:
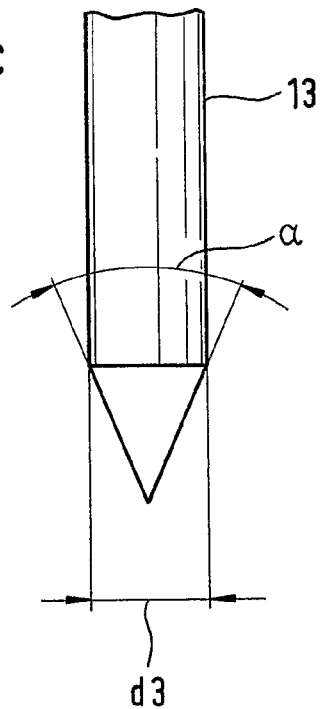
FIG. 3c shows a machining tool in the form of a diamond-coated grinder having a conical point.
Figure 3D:
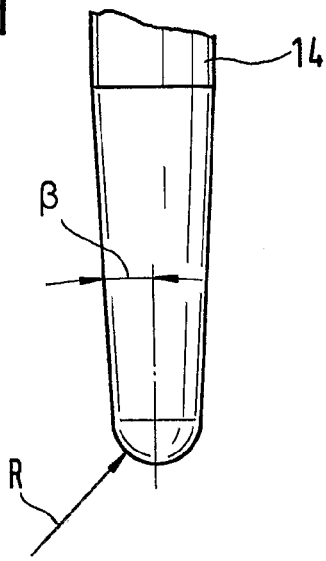
FIG. 3d shows a machining tool in the form of a diamond-coated grinder having a tapered portion and a rounded conical point.

With all blanks, it is essential that the position of the gages 4, 5 on the machining equipment is known or can be unambiguously determined. This can be done, for example, by scanning FIG. 3 shows machining tools as used for machining corpus 1. FIGS. 3a and 3b show a diamond-coated cylindrical grinder or milling cutter, with the grinder 11 of FIG. 3a exhibiting a first diameter d1 and the grinder 12 of FIG. 3b a second diameter d2. A grinder that is designed in this way is primarily used for machining interior spaces with vertical walls. FIGS. 3c and 3d each show a diamond-coated grinder 13, 14 that tapers to a point. In FIG. 3c, the end of the grinder 13 exhibits an angle α of 45°. In FIG. 3d the end of the grinder 14 is in the form of a cone, of which the point is rounded with a radius R. A grinder that is shaped in this way is primarily used for machining occlusion surfaces with fissures, as well as interior spaces with non-vertical walls.

Figure 3E:
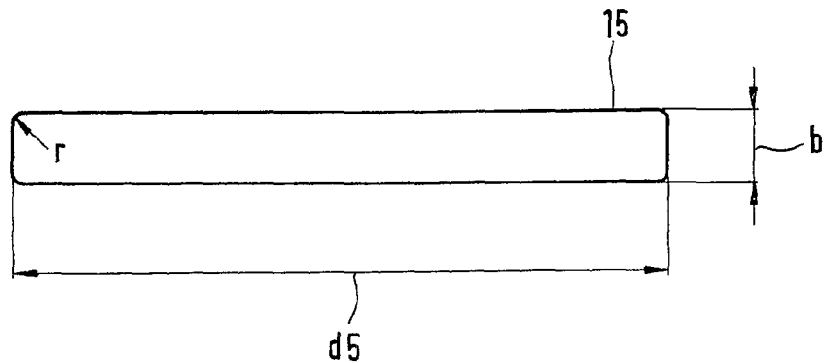
FIG. 3e shows a machining tool in the form of a diamond-coated grinding wheel.

FIG. 3e shows a diamond-coated grinding wheel 15, which is used for both separation and roughing as well as for carving down to final dimensions. The edges of the grinding wheel exhibit a radius r and the wheel has a diameter d5 and a width b.

FIG. 4 shows the machining tool of FIG. 3 engaged in a gage. FIGS. 4a and 4b show a diamond-coated cylindrical grinder 11, 12, and demonstrate how grinder 11 penetrates the bore-shaped gage 5 by a distance t1, whilst the other grinder 12, because of its larger diameter, cannot penetrate gage 5. The penetration depth t2 is in this case equal to zero, from which it can be ascertained that tool 12 is involved.

Figure 4A:
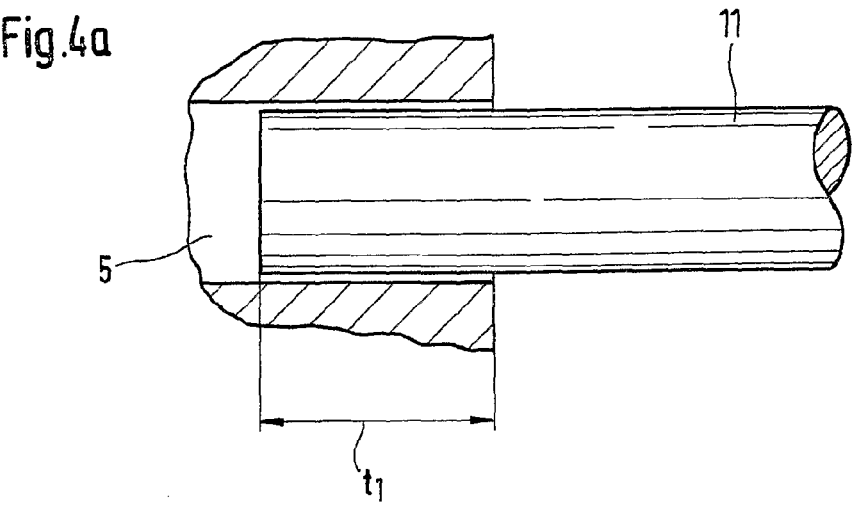
FIG. 4a shows a gage by means of which the machining tool of FIG. 3a is checked.
Figure 4B:
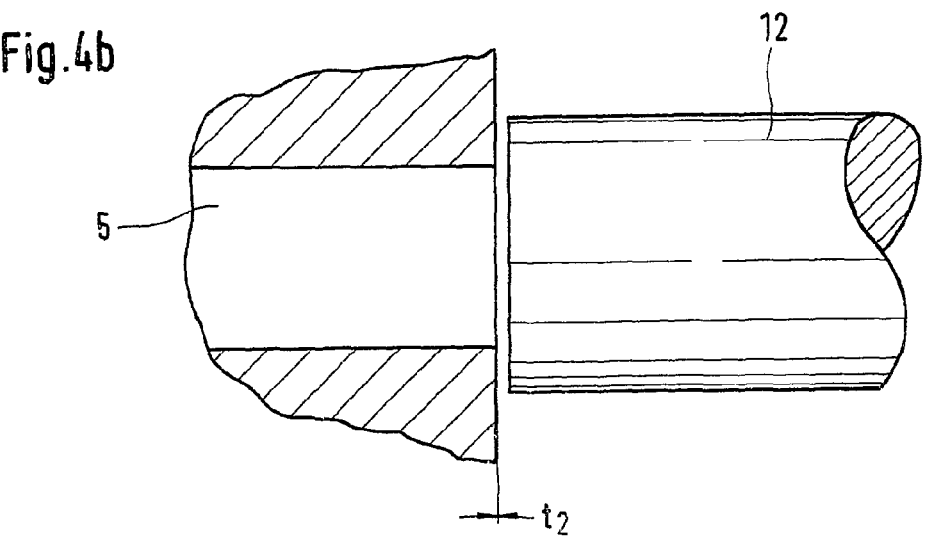
FIG. 4b shows a gage by means of which the machining tool of FIG. 3b is checked.
Figure 4C:
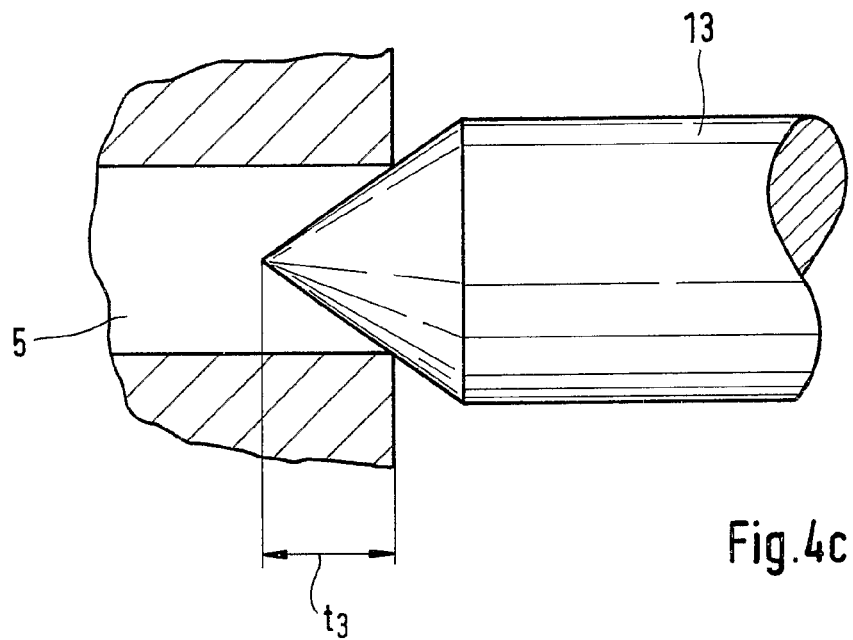
FIG. 4c shows a gage by means of which the machining tool of FIG. 3c is checked.
Figure 4D:
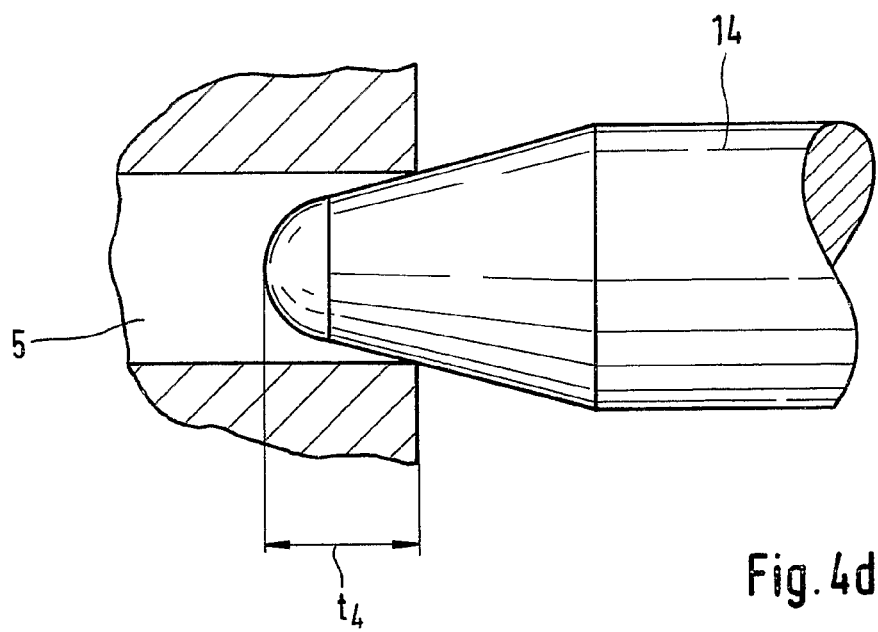
FIG. 4d shows a gage by means of which the machining tool of FIG. 3d is checked.

FIGS. 4c and 4d each show a diamond-coated grinder 13, 14 tapered to a tip as it penetrates gage 5 in the form of a bore. The penetrations illustrated in FIGS. 4c and 4d of a magnitude t3 in FIG. 4c and t4 in FIG. 4d, serve not only to determine the ideal outer contour and thus to define the type of tool, but also provide information on the wear condition and the suitability of the respective tool for the intended machining process.

Figure 4E:
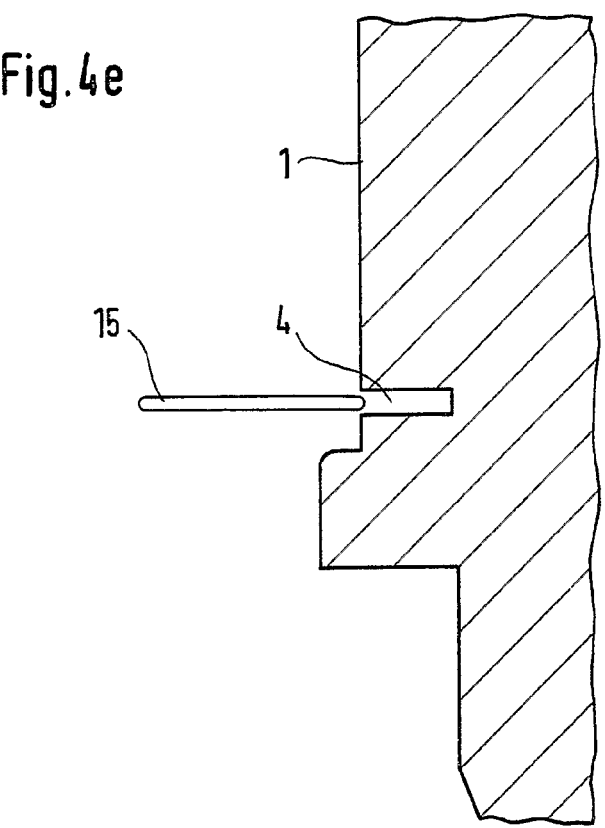
FIG. 4e shows a gage by means of which the machining tool of FIG. 3e is checked.

FIG. 4e shows a diamond-coated grinding wheel 15 at a point at which grinding wheel 15 is about to move into the groove-shaped gage 4 of FIG. 3e on corpus 1 of the blank. This moment of penetration provides information as to whether the grinding wheel is too thick and thus unsuitable for the scheduled grinding procedure.

Figure 4F:
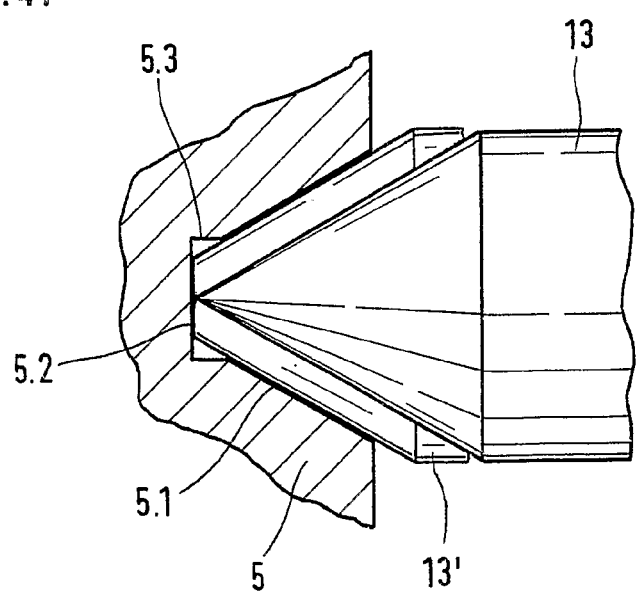
FIG. 4f shows a gage by means of which the wear condition of the machining tool of FIG. 3c is checked.

FIG. 4f shows a gage 5 that is used to detect the wear condition of the tool tip. The gage has a conical open region 5.1, which merges into a base region 5.2. Between them is a cylindrical region 5.3. Tool 13, when new, moves into the gage at its pointed end such that only the tip touches the base 5.2. If the tip is as worn out as on tool 13', then the depth of penetration of its pointed end up to the point of reaching the base 5.2 or up to the point of touching the side walls of the open region 5.1 will be greater than when tool 13 is new. The amount of wear can thus be inferred from this measurement.

Figure 5:
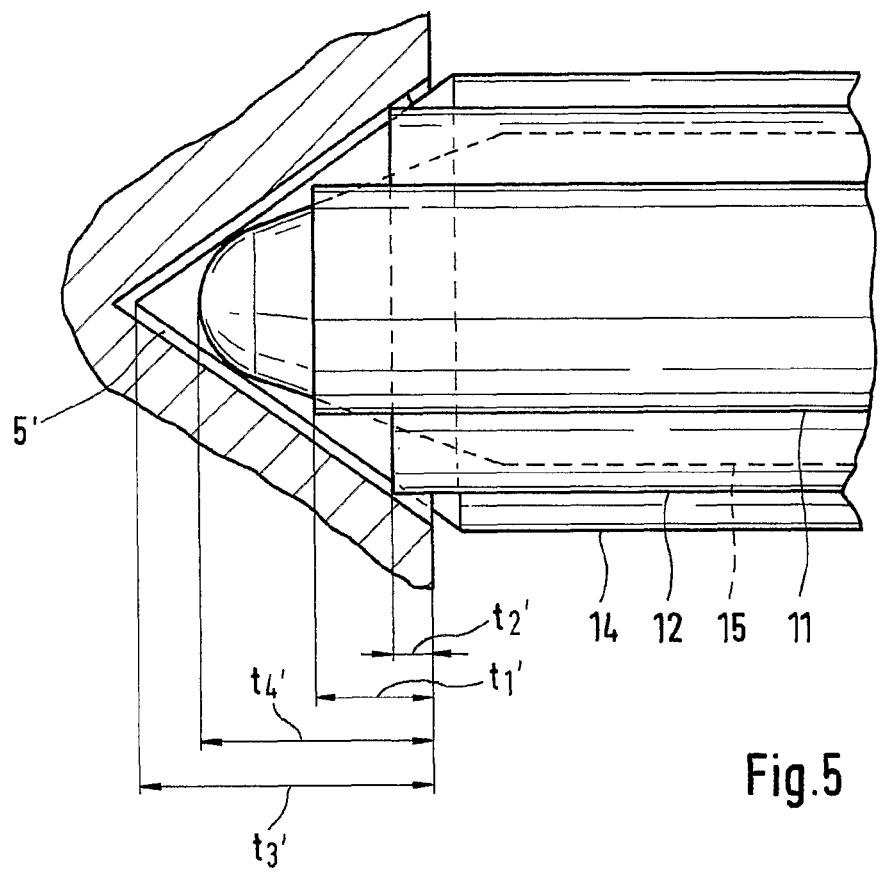
FIG. 5 shows a gage that is designed as a universal gage for checking several tools having various contours.

FIG. 5 shows a single cylindrical recess 5' for tools 11 to 14 shown in FIGS. 3a to 3d that is designed as a universal gage. The respective actual penetration depths t1', t2', t3', t4', provide information on the condition of the respective tool and thus on the suitability of the tool for the intended machining operation.

Figure 6:
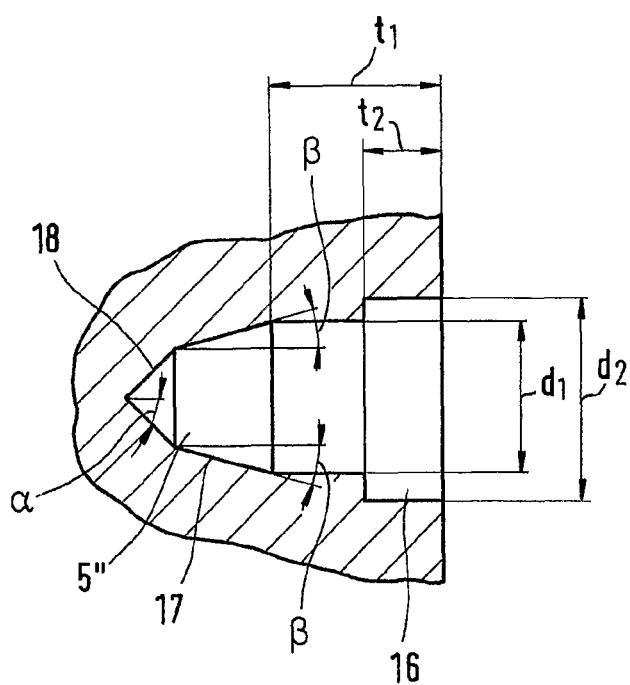
FIG. 6 shows a further embodiment of a gage suitable for use as a universal gage.
Figure 7A:
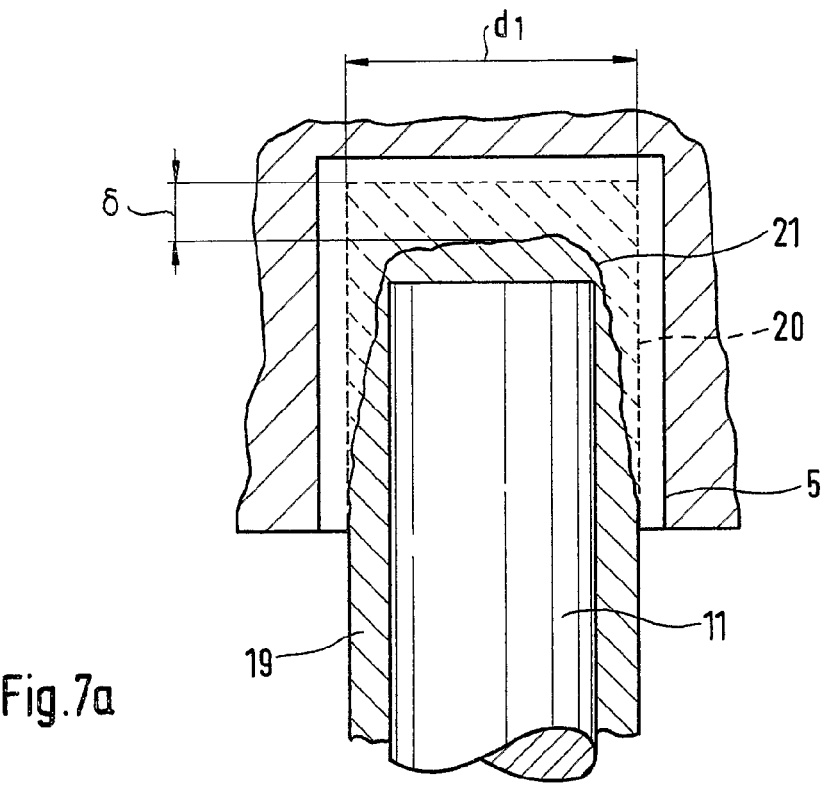
FIGS. 7a, 7b show wear measurement means for a cylindrical and conical grinder respectively.
Figure 7B:
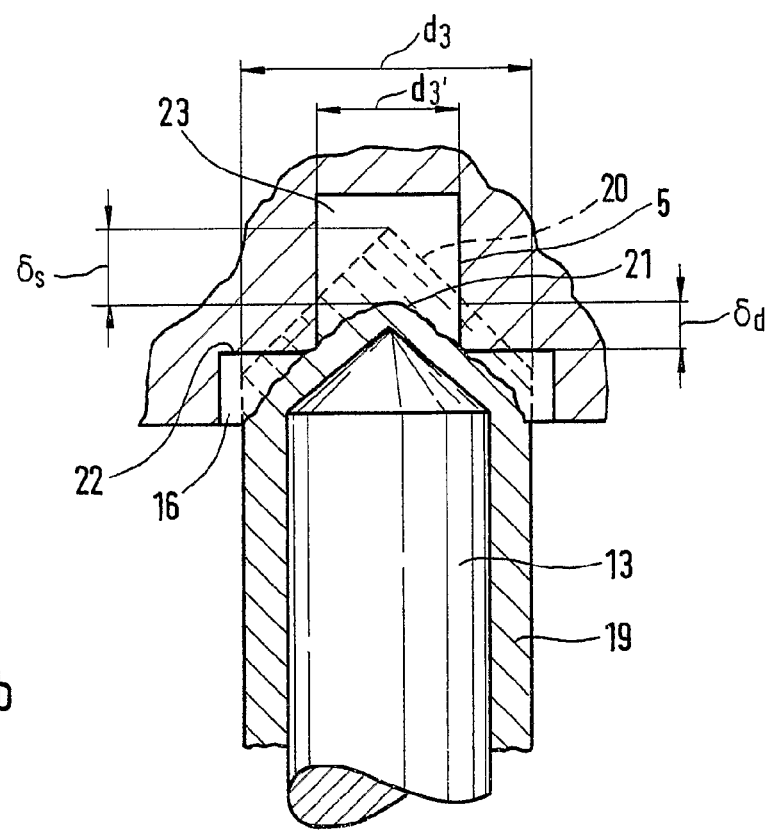

FIG. 6 shows a further single recess 5" serving as a universal gage. This recess includes a bore 16 having a diameter d2 and an associated possible penetration depth t2 and one having a diameter d1 and an associated possible penetration depth t2. In addition, the recess exhibits a taper 17 having a cone angle β and a further taper 18 having a cone angle α for the examination of corresponding tools. Alternatively, instead of one or more angles, one or more roundings having radii R (see FIG. 3d) that match the respective tools can be provided. The penetration depth achieved in each instance can yield information on the condition of the respective tool and thus the suitability thereof for the intended machining operation. FIGS. 7a and 7b show how wear measurement can be carried out. Tool 11 is furnished with a coating 19 that provides the actual cutting edges, for example the diamond coating of a grinding pin. This coating 19 exhibits an ideal outer contour 20, which is indicated by the dashed lines. However, due to the wear incurred during machining, the actual outer contour 21 of tool 11 will deviate from the ideal outer contour 20.

In the region of the end-cutting surface, the amount of wear of the coating 19 between the ideal outer contour 20 and the actual outer contour 21 is equal to the distance 6 which, with an original coating thickness of from 50 to 60 µm, can well amount to from 40 to 50 µm. The wear of the end-cutting surface can be determined by measuring the depth of penetration of tool 11 into gage 5. FIG. 7b shows how a gage 5 can be used for measurement of the wear of a coated conical grinder. The conical grinder has a coating 19, which again has an ideal outer contour 20 and an actual outer contour 21. Due to the bore 16, the diameter of the used tool 13 is first identified and, due to a stop limit surface 22 having a central bore 23, the wear $\delta_d$ of the envelope of the cone is determined. The wear $\delta_s$ of the cone tip can be determined in accordance with FIG. 7a, but can also be measured in accordance with FIG. 7b when certain empirical values are available. For the measurement of a truncated cone point, and also of a conical grinder, a separate gage can be provided for each diameter, and the wear measurement can, in each case, be carried out by measuring the depth of penetration into the gage.

What is claimed is:

1. A method for producing a dental shaped part, the method comprising:
    checking an outer contour of at least one tool of machining equipment, using at least one gauge provided on a blank formed from a tooth restoration material from which a dental shaped part is to be machined using the machining equipment, wherein the gauge is a recess, and wherein the checking includes:
        engaging at least part of the tool with the recess at a penetration depth in the recess, the penetration depth determining at least one of a condition of the tool and an ideal outer contour indicating a type of the tool, and removing the at least part of the tool from the recess; and machining the dental shaped part from the blank by using the tool of the machining equipment, checked in the checking, to remove material from the blank, when the outer contour of the tool corresponds to the at least one gauge provided on the blank.

2. The method as defined in claim 1, wherein the tool of the machining equipment is one of a first tool and a second tool, and a diameter of an end of the first tool is smaller than a diameter of an end of the second tool, the recess has at least one predetermined dimension and shape, the end of the first tool fits into the recess, and at least a portion of the recess is smaller in size than the diameter of the second tool, said dental shaped part is machined from the blank by using at least one of the first and second tools to remove material from the blank, and the checking includes engaging at least part of at least one of the first and second tools with the recess at a penetration depth in the recess and removing the at least part of the at least one of the first and second tools from the recess, the penetration depth determining at least one of a condition of the at least one of the first and second tools and an ideal outer contour indicating a type of the at least one of the first and second tools.

3. The method as defined in claim 2, wherein the blank has a handle for positioning a corpus of the blank in machining equipment, and the recess is provided on the handle.

4. The method as defined in claim 3, wherein the recess is located on the corpus.

5. The method as defined in claim 2, wherein the gauge distinguishes an outer contour of the first tool from an outer contour of the second tool.

6. The method as defined in claim 2, wherein the shape of the recess is cylindrical and a diameter of the recess is smaller than the diameter of the second tool.

7. The method as defined in claim 2, wherein the recess is tapered to correspond at least in part to an outer contour of the first tool and the recess tapers to a diameter which is smaller than the diameter of the second tool.

8. The method as defined in claim 2, wherein the recess is in the form of a groove or a bore.

9. The method as defined in claim 2, wherein the recess identifies a state of permissible allowance of the first tool when the first tool engages the recess.

10. The method as defined in claim 2, wherein the gauge functions as a universal gauge for prospective tools.

11. The method as defined in claim 2, wherein the gauge of the blank is one of a plurality of gauges, each of the plurality of gauges being designed as a recess having dimensions and a shape that correspond at least in part to an outer contour of one of the first tool or the second tool.

12. The method as defined in claim 2, wherein the gauge has a first diameter of an outer contour of the first tool, and an outer contour of the second tool does not fit into the gauge.

13. The method as defined in claim 1, further comprising:

driving the tool into the at least one gauge provided on the blank; and determining an actual state of a permissible allowance of the tool.

14. The method as defined in claim 13, further comprising:

determining a degree of deviation of the actual state of the permissible allowance of the tool from an ideal outer contour of the tool; and controlling the machining of the dental shaped part from the blank based on the determined degree of deviation.

* * * * *